US012679936B2

(12) United States Patent
Nguyen et al.

(10) Patent No.: US 12,679,936 B2
(45) Date of Patent: Jul. 14, 2026

(54) RARE-EARTH CATALYSED POLYISOPRENE ARTICLES

(71) Applicant: LifeStyles Healthcare Pte. Ltd., Singapore (SG)

(72) Inventors: KC Nguyen, A. Phunphin (TH); Chayapon Ngowprasert, A. Phunphin (TH); Chintana Netrung, A. Phunphin (TH); Atip Boonbumrung, A. Phunphin (TH); Phetcharat Rabingkao, A. Phunphin (TH)

(73) Assignee: LifeStyles Healthcare Pte. Ltd., Singapore (SG)

( * ) Notice: Subject to any disclaimer, the term of this patent is extended or adjusted under 35 U.S.C. 154(b) by 215 days.

(21) Appl. No.: 18/279,495

(22) PCT Filed: Mar. 2, 2022

(86) PCT No.: PCT/SG2022/050109
§ 371 (c)(1),
(2) Date: Aug. 30, 2023

(87) PCT Pub. No.: WO2022/186778
PCT Pub. Date: Sep. 9, 2022

(65) Prior Publication Data
US 2024/0150529 A1 May 9, 2024

Related U.S. Application Data

(60) Provisional application No. 63/155,959, filed on Mar. 3, 2021.

(30) Foreign Application Priority Data

Jan. 12, 2022 (AU) ................................ 2022900058

(51) Int. Cl.
*A61F 6/04* (2006.01)
*C08C 19/20* (2006.01)
(Continued)

(52) U.S. Cl.
CPC ..................................... *C08J 5/02* (2013.01); *A61F 6/04* (2013.01); *C08C 19/20* (2013.01); *C08F 136/08* (2013.01); *C08J 3/24* (2013.01); *C08J 2309/10* (2013.01)

(58) Field of Classification Search
CPC ..... A61F 6/04; A61B 42/10; C08J 3/24; C08J 2309/10; C08F 136/08; C08F 4/12; C08F 36/08; A41D 13/087; C09D 109/10
See application file for complete search history.

(56) References Cited

U.S. PATENT DOCUMENTS 6,828,387 B2 12/2004 Wang et al.
8,087,412 B2 1/2012 Lucas et al.
(Continued)

FOREIGN PATENT DOCUMENTS

CN 101280033 A 10/2005
CN 101608003 A 12/2009
(Continued)

OTHER PUBLICATIONS

PCT International Search Report in PCT/SG2022/050109 dated Mar. 24, 2022, 8 pages.
(Continued)

*Primary Examiner* — Ophelia A Hawthorne
(74) *Attorney, Agent, or Firm* — Servilla Whitney LLC

(57) ABSTRACT

Disclosed herein is a polymeric article having an elastomeric layer including cured synthetic polyisoprene particles that include a rare earth catalysed polyisoprene. The polyisoprene particles may include sulfur crosslinks and/or may be pre-vulcanized. Also disclosed herein are methods for pro-
(Continued)

ducing polymeric articles having an elastomeric layer including cured synthetic polyisoprene particles that include a rare earth catalysed polyisoprene.

11 Claims, 7 Drawing Sheets

(51) Int. Cl.

| | | |
|---|---|---|
| *C08F 136/08* | (2006.01) | |
| *C08J 3/24* | (2006.01) | |
| *C08J 5/02* | (2006.01) | |

(56) References Cited

U.S. PATENT DOCUMENTS

| | | | |
|---|---|---|---|
| 8,464,719 | B2 | 6/2013 | Lucas |
| 2015/0368383 | A1 | 12/2015 | Kaita et al. |
| 2019/0031788 | A1 | 1/2019 | Kodemura |
| 2019/0062471 | A1 | 2/2019 | Nguyen et al. |

FOREIGN PATENT DOCUMENTS

| | | | | |
|---|---|---|---|---|
| CN | 102532354 | A | 7/2012 | |
| CN | 107226916 | A | 10/2017 | |
| CN | 109233031 | A | 1/2019 | |
| EP | 0204373 | A | 12/1986 | |
| EP | 2650313 | A1 | 10/2013 | |
| EP | 2857422 | A1 | 4/2015 | |
| EP | 2824118 | B1 | 12/2017 | |
| WO | WO-2019173863 | A1 * | 9/2019 | ............ C08L 19/003 |
| WO | 2020043268 | A1 | 3/2020 | |

OTHER PUBLICATIONS

Abstract of Article from Changchun Institute of Applied Chemistry, Chinese Academy of Sciences (CIAC, CAS).
Abstract of Article from Chemistry A European Journal / vol. 25, Issue 10.
"Machine translation of CN101608003A".
"Machine translation of CN107226916A".
"Machine translation of CN109233031A".

* cited by examiner

RARE-EARTH CATALYSED POLYISOPRENE ARTICLES

CROSS-REFERENCE TO RELATED APPLICATIONS

This application is a National Phase entry of International Application No. PCT/SG2022/050109, filed Mar. 2, 2022, which claims priority to Australian Provisional Patent Application No. 2022900058, filed Jan. 12, 2022, and U.S. Provisional Patent Application No. 63/155,959, filed Mar. 3, 2021, the disclosures of which are incorporated herein by reference in their entireties.

TECHNICAL FIELD

The present disclosure is directed to polymeric articles comprising polyisoprene catalysed by rare earth metal catalysts. In particular, personal protective devices and, more specifically, gloves and condoms, comprise elastomeric layers of cured, pre-vulcanized synthetic polyisoprene particles made from polyisoprene catalysed by rare earth metal catalysts.

BACKGROUND

Personal protective and medical devices, such as: condoms; finger cots; contraceptive diaphragms; gloves, such as examination and surgical gloves; medical devices, such as catheter tubing and catheter balloons, are typically made of polymeric materials to provide protection against chemicals, abrasions, germs, viruses, and microbes among many uses. Polymeric materials include natural rubber latex (natural polyisoprene), synthetic polyisoprene, or various polyurethanes. Prophylactic devices made of natural rubber are strong. Natural rubber, sourced from *Hevea brasiliensis* and/or guayule, has a high level of stereo-regularity. Of the polyisoprene polymer content of natural rubber latex, about 98% by weight is cis-1,4 isoprene units and about 2% by weight is trans-1,4 isoprene units. Natural rubber latex is also a highly branched polymer with a high molecular weight and a wide molecular weight distribution. These characteristics of the natural rubber result in vulcanized rubber products having a unique combination of strength and elasticity. However, natural rubber also contains proteins that produce dermal allergic reactions in some susceptible individuals.

Synthetic polyisoprene resins have been developed to provide benefits of natural rubber and to eliminate a potential for protein allergy. Some synthetic polyisoprenes, such as that produced by anionic addition polymerization, typically consist of lower levels of stereo-regularity (i.e., ~90-92% cis-1,4 isoprene) and reduced molecular weight. Other synthetic polyisoprenes, such as those produced by Ziegler-Natta catalyst (titanium-aluminium catalyst), can provide higher molecular weight and higher cis-structure (i.e., ~96-98.5% cis-1,4 isoprene) but are susceptible to crystallization, high gel content, and high ash content.

Consequently, articles produced from such synthetic polyisoprenes can still have some inferior properties compared with natural rubber articles.

There is an ongoing need to produce articles such as personal protective devices and, more specifically, personal protective devices such as condoms, finger cots, and polymeric gloves that are thin, strong and non-allergenic.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each of the appended claims.

SUMMARY

Disclosed herein is a polymeric article comprising:

an elastomeric layer comprising pre-vulcanized cured synthetic polyisoprene particles that comprise: a plurality of sulfur crosslinks and a rare earth catalysed polyisoprene material comprising a cis-1,4 isomer content of greater than 97.0% by weight and a rare earth element content of greater than or equal to 0.1 mg/kg and less than or equal to 100 mg/kg, wherein the synthetic polyisoprene particles are pre-vulcanized.

Also disclosed herein is a condom comprising:

an elastomeric layer comprising cured synthetic polyisoprene particles that are pre-vulcanized and comprise sulfur crosslinks;

wherein the synthetic polyisoprene particles comprise a rare earth catalysed polyisoprene material that comprises:

a cis-1,4 isomer content of greater than 97.0% by weight; a trans-1,4 isomer content of 1% by weight or less; and a 3,4 isomer content of 1% by weight or less.

Also disclosed herein is a method for producing a polymeric article, comprising:

pre-vulcanizing an emulsion comprising a rare earth catalysed polyisoprene material comprising a cis-1,4 isomer content of greater than 97.0% by weight; disposing an elastomeric coating of the emulsion comprising the rare earth catalysed polyisoprene material on a former; and curing the elastomeric coating to form an elastomeric layer of the polymeric article, wherein the elastomeric layer comprises cured synthetic polyisoprene particles cross-linked by sulfur and a rare earth element content of greater than or equal to 0.1 mg/kg and less than or equal to 100 mg/kg.

Also disclosed herein is a polymeric article produced by a method described herein.

Embodiments according to the present disclosure include polymeric articles, and methods for manufacturing polymeric articles, that comprise synthetic polyisoprene materials catalysed using rare earth catalysts, for example substantially as shown in and/or described in connection with at least one of the figures, as set forth more completely in the claims, are disclosed. Various advantages, aspects, and novel features of the present disclosure will be more fully understood from the following description and drawings.

The foregoing summary is not intended, and should not be contemplated, to describe each embodiment or every implementation of the present disclosure. Other and further embodiments are described below.

It will be appreciated that the embodiments of each aspect of the present disclosure may equally be applied to each other aspect, mutatis mutandis.

BRIEF DESCRIPTION OF DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only typical embodiments of this disclosure and are therefore not to be considered limiting of its scope, for the disclosure may admit to other equally effective embodiments. It is to be understood that elements and features of one embodiment may be in other embodiments without further recitation. It is further understood that, where possible, identical reference numerals have been used to indicate comparable elements that are common to the figures.

DESCRIPTION OF EMBODIMENTS

Terms and Definitions

Figure 1:
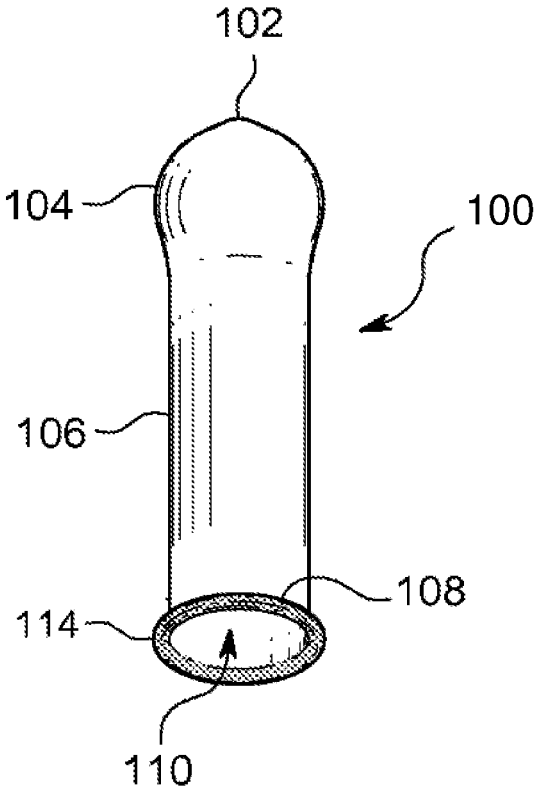
FIG. 1 is a perspective schematic view of a condom according to an embodiment.

Before describing embodiments of the present disclosure in detail, the terminology used herein is for the purpose of describing particular embodiments only, and is not intended to be limiting. The embodiments described herein should not necessarily be limited to specific compositions, materials, designs or equipment, as such may vary. All technical and scientific terms used herein have the usual meaning conventionally understood by persons skilled in the art to which this disclosure pertains, unless context defines otherwise.

The definitions are provided to aid in describing particular embodiments, and are not intended to limit the claimed invention, because the scope of the invention is limited only by the claims.

All references, including publications, patent applications, and patents, cited herein, unless described otherwise, are hereby incorporated by reference to the same extent as if each reference were individually and specifically indicated to be incorporated by reference and were set forth in its entirety herein.

Unless otherwise required by context, singular terms shall include pluralities and plural terms shall include the singular. Throughout this disclosure, unless specifically stated otherwise or the context requires otherwise, reference to a single step, composition of matter, group of steps or group of compositions of matter shall be taken to encompass one and a plurality (i.e., one or more) of those steps, compositions of matter, groups of steps or groups of compositions of matter. Thus, as used herein, the singular forms "a", "an" and "the" include plural aspects unless the context clearly dictates otherwise. For example, reference to "a" includes a single as well as two or more; reference to "an" includes a single as well as two or more; reference to "the" includes a single as well as two or more and so forth.

Those skilled in the art will appreciate that the disclosure herein is susceptible to variations and modifications other than those specifically described. It is to be understood that the disclosure includes all such variations and modifications. The disclosure also includes all of the examples, steps, features, methods, compositions, formulations, and processes, referred to or indicated in this specification, individually or collectively, and any and all combinations or any two or more of said steps or features.

The term "and/or", e.g., "X and/or Y" shall be understood to mean either "X and Y" or "X or Y" and shall be taken to provide explicit support for both meanings or for either meaning.

Unless otherwise indicated, the terms "first," "second," etc. are used herein merely as labels, and are not intended to impose ordinal, positional, or hierarchical requirements on the items to which these terms refer. Moreover, reference to a "second" item does not require or preclude the existence of lower-numbered item (e.g., a "first" item) and/or a higher-numbered item (e.g., a "third" item).

As used herein, the phrase "at least one of" or "one or more of" when used with a list of items, means different combinations of one or more of the listed items may be used and only one of the items in the list may be needed. The item may be a particular object, thing, or category. In other words, "at least one of" means any combination of items or number of items may be used from the list, but not all of the items in the list may be required. For example, "at least one of item A, item B, and item C" may mean item A; item A and item B; item B; item A, item B, and item C; or item B and item C. In some cases, "at least one of item A, item B, and item C" may mean, for example and without limitation, two of item A, one of item B, and ten of item C; four of item B and seven of item C; or some other suitable combination.

It is to be appreciated that certain features that are, for clarity, described herein in the context of separate embodiments, may also be provided in combination in a single embodiment. Conversely, various features that are, for brevity, described in the context of a single embodiment, may also be provided separately or in any sub-combination.

Throughout the present specification, various aspects and components of the disclosure can be presented in a range format. The range format is included for convenience and should not be interpreted as an inflexible limitation on the scope of the present disclosure. Accordingly, the description of a range should be considered to have specifically disclosed all the possible sub-ranges as well as individual numerical values within that range, unless specifically indicated. For example, description of a range such as from 1 to 5 should be considered to have specifically disclosed sub-ranges such as from 1 to 3, from 1 to 4, from 1 to 5, from 2 to 4, from 2 to 5, from 3 to 5 etc., as well as individual and partial numbers within the recited range, for example, 1, 2, 3, 4, 4.5 and 5, unless where integers are required or implicit from context. This applies regardless of the breadth of the disclosed range. Where specific values are required, these will be indicated in the specification.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Throughout this specification, the term "consisting essentially of" is intended to exclude elements which would materially affect the properties of the claimed composition, although may include elements that do not materially affect properties.

The terms "comprising", "comprise" and "comprises" herein are intended to be optionally substitutable with the terms "consisting essentially of", "consist essentially of", "consists essentially of", "consisting of", "consist of" and "consists of", respectively, in every instance.

Herein, unless indicated otherwise, the term "about" encompasses a 10% tolerance in any value or values connected to the term.

The terms "emulsion", "dispersion", "latex" and "suspension" are generally analogous and indicate a system in which small particles of a substance, such as rubber particles, are mixed with a fluid solvent (such as water and/or alcohols and/or other organic fluids) but are at least partially undissolved and kept dispersed by agitation (mechanical suspension) and/or by the molecular forces in a surrounding medium (colloidal suspension). Emulsions contemplated herein may further comprise typical and suitable components for rubber or elastomeric formulations and compounds, such as accelerators, such as, for example: guanidines, thiazoles, thiurams, sulfenamides, thioureas, dithiocarbamates, and xanthates. Depending on a specific application, exemplary non-limiting examples of accelerators may include one or more of: hexamethylene tetramine (HMT), heptaldehyde-aniline condensation product (BA), diphenyl guanidine (DPG), N,N'-diorthotolyl guanidine (DOTG), 2-mercaptobenzothiazole (MBT), 2-2'-dithiobis (benzothiazole) (MBTS), zinc-2-mercaptobenzothiazole (ZMBT), zinc-O,O-di-N-phosphorodithioate (ZBDP), N-cyclohexyl-2-benzothiazole sulfenamide (CBS), N-tert-butyl-2-benzothiazole sulfenamide (TBBS), 2-(4-morpholinothio)-benzothiazole (MBS), N,N'-dicyclohexyl-2-benzothiazole sulfenamide (DCBS), ethylene thiourea (ETU), di-pentamethylene Thiourea (DPTU), dibutyl thiourea (DBTU), tetramethylthiuram monosulfide (TMTM), tetramethylthiuram disulfide (TMTD), dipentamethylenethiuram tetrasulfide (DPTT), tetrabenzylthiuram disulfide (TBzTD), zinc dimethyldithiocarbamate (ZDMC), zinc diethyldithiocarbamate (ZDEC), zinc dibutyldithiocarbamate (ZDBC), zinc dibenzyldithiocarbamate (ZDBC), and/or zinc-isopropyl xanthate (ZIX). Emulsions contemplated herein may further comprise activators, such as zinc oxides, cross-linking agents and curatives, such as elemental sulfur, monosulphidic donors, di-sulphidic donors, such as tetramethyl thiuram disulphide and tetraethyl thiuram disulphide; and/or polysulphidic donors, such as xanthogen polysulphide and dipentamethylene thiuramtetrasulfide. Emulsions contemplated herein may further comprise anti-oxidants and/or anti-ozonants. Phenolic antioxidants may be used. At least one suitable anti-oxidant is butylated reaction product of p-cresol and dicyclopentadiene (Wingstay L). Emulsions contemplated herein may further comprise, surfactants, such as sodium dodecyl sulfates and polyvinyl alcohols. Emulsions contemplated herein may further comprise rheology-modifiers, such as various clays and aluminosilicates, pH adjusters, such as hydroxides, such as potassium hydroxide, pigments, processing agents, and/or fillers as are known to those in the art.

The term "polymer" generally includes, but is not limited to, homopolymers, copolymers, such as for example, block, graft, random and alternating copolymers, terpolymers, etc. Furthermore, unless otherwise specifically limited, the term "polymer" includes all possible geometrical configurations of the molecule. These configurations include, but are not limited to isotactic, syndiotactic and random symmetries.

The term "thermoplastic" generally includes polymer materials that become reversibly pliable, mouldable, and heatable above a specific temperature and solidify upon cooling. The term "thermoset" generally includes polymer materials that strengthen following heating and solidification, and cannot be reheated and re-formed after an initial forming. The term "thermoplastic elastomer" (TPE) denotes a class of copolymers comprising both thermoplastic and thermoset moieties, producing materials having properties of both moieties. The term "rubber" generally indicates elastomers produced from natural rubber latexes or synthetic elastomers.

Polyisoprene Articles

Embodiments described in this disclosure, briefly summarised above and discussed in greater detail below, comprise polymeric articles, including articles, for example personal protective equipment such as gloves, and condoms, including thin-walled condoms. Some embodiments may comprise gloves or condoms that are formed without using coagulants. Other embodiments may comprise gloves or condoms that are formed using coagulants. Embodiments may comprise gloves that are made using rare earth catalysed synthetic polyisoprene materials. Embodiments may comprise condoms that are formed using rare earth catalysed synthetic polyisoprene materials. Embodiments may comprise condoms that are made using rare earth catalysed synthetic polyisoprene materials and the absence of coagulants. If used, a coagulant system may be formulated with one or more salts, such as, but not limited to, calcium nitrate, calcium chloride, calcium citrate, and/or aluminium sulfate. These salts may be present in a range of about 5 to about 40%, for example about 5 to about 25% and/or in an amount equal to, equal to about, or at least about: 5, 10, 15, 20, 25, 30, 35, or 40%. The coagulant system may also comprise one or more anti-tacking agents, such as calcium carbonate, silica and/or calcium stearate. The one or more anti-tacking agents may be present in a range of about 1 to about 10%, for example in an amount equal to, equal to about, or at least about: 1, 2, 3, 4, 5, 6, 7, 8, 9 or 10%. The coagulant system may also comprise one or more surfactants or wetting agents, such as one or more surfactants comprising ethoxylate and/or sulfonate groups. The one more surfactants and/or wetting agents may be present in an amount in a range of about at 0.05 to about 2.0%, for example in an amount equal to, equal to about, or at least about: 0.05, 0.1, 0.2, 0.4, 0.6, 0.8, 1.0, 1.2, 1.4, 1.6, 1.8, or 2.0%. The coagulant system may also comprise one or more anti-foaming agents in an amount of about 0.01 to about 0.1%, for example in an amount equal to, equal to about, or at least about: 0.01, 0.02, 0.03, 0.04, 0.05, 0.06, 0.07, 0.08, 0.09 or 0.1%. The coagulant system may comprise water.

An article described herein, for example a condom, may be tested to identify and/or quantify a particular characteristic utilising a known standard known in the art, for example one or more of: ISO 23409:2011, ISO4074:2015, ASTM D3492-16, SS EN ISO 17294-1:2004, ISO 17294-2:2016 and/or US EPA Method 200.8 Revision 5.4, 1994.

An article described herein may be analysed to assess and/or quantify one more characteristics, for example one or more of: burst pressure, burst volume, force at break, tensile strength, and/or elongation at break.

In one embodiment the burst pressure of an article defined herein may be in a range of about 1.0 kPa to about 1.5 kPa, for example measured according to one or more of ISO 23409:2011, ISO4074:2015, and/o ASTM D3492-16. In another embodiment the burst pressure of the article is, is about, at least, or at least about: 0.80, 0.85, 0.90, 0.95, 1.00, 1.05, 1.10, 1.15, 1.20, 1.25, 1.30, 1.35, 1.40, 1.45, or 1.50 kPa.

In one embodiment the burst volume of an article defined herein may be equal, equal to about, at least, or at least about: 27.5 L, 30.0 L, 32.5 L, 35.0 L, 37.5 L, 40.0 L, 42.5 L, 45.0 L, 47.5 L, 50.0 L, 52.5 L, 55.0 L, 57.5 L or 60.0 L. The burst volume may be measured according to one or more of ISO 23409:2011, ISO4074:2015, and/or ASTM D3492-16.

In one embodiment the force at break of an article defined herein may be equal, equal to about, at least, or at least about: 40 N, 45 N, 50 N, 55 N, 60 N, 65 N, 70 N, 75 N, 80 N, 85 N, 90 N, 95 N, 100 N, 105 N, 110 Nor 115 N. The force at break may be measured according to one or more of ISO 23409:2011, ISO4074:2015, and/or ASTM D3492-16.

In one embodiment the tensile strength of an article defined herein may be equal, equal to about, at least, or at least about: 10 kPa, 11 kPa, 12 kPa, 13 kPa, 14 kPa, 15 kPa, 16 kPa, 17 kPa, 18 kPa, 19 kPa, 20 kPa, 21 kPa, 22 kPa, 23 kPa, 24 kPa, 25 kPa, 26 kPa, 27 kPa, 28 kPa, 29 kPa, 30 kPa, 31 kPa, 32 kPa, 33 kPa, 34 kPa, or 35 kPa. The tensile strength may be measured according to one or more of ISO 23409:2011, ISO4074:2015, and/or ASTM D3492-16.

In one embodiment the elongation at break of an article defined herein may be equal, equal to about, at least, or at least about: 700%, 725%, 750%, 775%, 800%, 825%, 850%, 875%, 900%, 925%, 950%, 975%, 1000%, 1025%, 1050%, 1075%, or 1100%. The elongation at break may be measured according to one or more of ISO 23409:2011, ISO4074:2015, and/or ASTM D3492-16.

In one or more embodiments, the polymeric articles comprise cured synthetic polyisoprene particles that comprise a rare earth catalysed polyisoprene material, the cured synthetic polyisoprene particles being cross-linked by sulfur. In one or more embodiments, a polymeric article comprises rare earth-catalysed polyisoprene particles that comprise intra-polyisoprene particle sulfur-crosslinks; inter-polyisoprene particle sulfur-crosslinks; or both intra-polyisoprene particle sulfur-crosslinks; inter-polyisoprene particle sulfur-crosslinks. In one or more embodiments, cured synthetic rare earth-catalysed polyisoprene particles of the inventive polymeric articles comprise both intra-polyisoprene particle sulfur-crosslinks and inter-polyisoprene particle sulfur-crosslinks. In one or more embodiments, the synthetic polyisoprene particles are bonded to each other by inter-polyisoprene particle sulfur-crosslinks. In one or more embodiments, the intra-polyisoprene particle sulfur-crosslinks and the inter-polyisoprene particle sulfur-crosslinks are uniform in the polymeric articles.

In one or more embodiments, about, at least, or at least about: 5%, 10%, 15%, 20%, 25%, 30%, 35%, 40%, 45%, 50%, 55%, 60%, 65%, 70%, 75%, 80%, 85%, 90%, or 95% of the polyisoprene particles, for example rare earth catalysed polyisoprene particles, used in the formation of an article (for example a glove and/or condom), are pre-vulcanized, for example pre-vulcanized to introduce intra-polyisoprene particle crosslinks such as sulfur crosslinks. The "%", may be a numerical fraction, w/w % or w/v %.

In one or more embodiments, less than, or less than about: 95%, 90%, 85%, 80%, 75%, 70%, 65%, 60%, 55%, 50%, 45%, 40%, 35%, 30%, 25%, 20%, 15%, 10%, 9%, 8%, 7%, 6%, or 5%, of the polyisoprene particles, for example rare earth catalysed polyisoprene particles, used in the formation of an article (for example a glove and/or condom), are not pre-vulcanized, for example to introduce intra-polyisoprene particle crosslinks, such as sulfur crosslinks. The "%", may be a numerical fraction, w/w % or w/v %.

In one or more embodiments the sulfur crosslinking, for example intra and/or inter polyisoprene particle crosslinking, may comprise, mono-sulfidic, di-sulfidic, or poly-sulfidic crosslinks. Herein, the poly-sulfidic crosslinks comprise at least 3 sulfur atoms. In yet another embodiment, about, at least, or at least about: 5%, 10%, 15%, 20%, 25%, 30%, 35%, 40%, 45%, 50%, 55%, 60%, 65%, 70%, 75%, 80%, 85%, 90%, or 95% of the intra- and/or inter polyisoprene particle crosslinking comprises mono-sulfidic, di-sulfidic, and/or poly-sulfidic crosslinks.

In one or more embodiments, the polymeric article (for example a glove or condom), comprises post-vulcanized composition comprising pre-vulcanized synthetic polyisoprene particles present in an amount of, about, at least, or at least about: 5%, 10%, 15%, 20%, 25%, 30%, 35%, 40%, 45%, 50%, 55%, 60%, 65%, 70%, 75%, 80%, 85%, 90%, or 95% of the polyisoprene particles. The "%", may be a numerical fraction, w/w % or w/v %.

While prior art condoms made of anionic polyisoprene rubber can present advantages of no residual monomer (100% conversion) and a colourless product, a disadvantage is low content of cis-1,4-structure of 90-92% by weight. In addition, prior art condoms made of Ziegler-Natta polyisoprene can have disadvantages of being susceptible to one or more of: crystallisation, high gel content, and/or high ash content.

Polymeric articles, including gloves and condoms disclosed herein made of rare-earth polyisoprene rubber may provide advantages of: the simple polymerisation process; stable gel-forming quality; low ash and/or gel content; and/or a cis 1,4-content of greater than or equal to 97% by weight, including greater than or equal to 97.5% by weight, greater than or equal to 98% by weight, greater than or equal to 98.5% by weight, greater than or equal to 99% by weight, and greater than or equal to 99.5% by weight. Herein the gel % wt may be less than about: 10, 9, 8, 7, 6, 5, 4, 3, 2, 1, 0.5% wt. In one embodiment, the gel % wt may be negligible or intrinsically nil. Herein the ash % wt may be less than about: 3.0, 2.5, 2.0, 1.5, 1.0, 0.5, 0.4, 0.3, 0.2, 0.1, 0.05% wt. In one embodiment, the ash % wt may be negligible or intrinsically nil.

The polyisoprene rubber used herein, for example in the formation of one more articles as described herein, may have a viscosity of less than about 150 cps, for example in a range of about 90 to about 120 cps. In one embodiment, the polyisoprene rubber used herein, for example in the form of a resin, has a viscosity of less than, or less than about: 150 cps, 145 cps, 140 cps, 135 cps, 130 cps, 125 cps, 120 cps, 115 cps, 110 cps, 105 cps, 100 cps, 95 cps, 90 cps, 85 cps, 80 cps, 75 cps, 70 cps, 65 cps, 60 cps, 55 cps, or 50 cps.

The polyisoprene rubber used herein may comprise residual solvent, for example one or more organic solvents used in the formation of the polyisoprene rubber. In one embodiment the isoprene rubber comprises less than, or less than about: 1500 ppm, 1250 ppm, 1000 ppm, 750 ppm, 500 ppm, 250 ppm, 100 ppm, or 50 ppm, of one or more solvents.

In one embodiment the rare-earth polyisoprene rubber may have a cis 1,4-content equal to, equal to about, at least, or at least about: 97.0%, 97.1%, 97.2%, 97.3%, 97.4%, 97.5%, 97.6%, 97.7%, 97.8%, 97.9%, 98.0%, 98.1%, 98.2%, 98.3%, 98.4%, 98.5%, 98.6%, 98.7%, 98.8%, 98.9%, 99.0%, 99.1%, 99.2%, 99.3%, 99.4%, or 99.5%.

The inventors have unexpectedly observed that polymeric articles such as condoms made from the rare earth catalysed polyisoprene resins described herein can have enhanced properties. For example, with a higher cis content (>97, and in some embodiments specifically >99%), the rare earth catalysed polyisoprene resins will have more crosslink availability and yield higher physical property than polyisoprene resins with lower cis content (for example, anionic polymerization and Zeigler Natta polymerization). Any, all or some of the embodiments according to the disclosure comprise condoms having a thickness of, for example, 0.050-0.075 mm in cross-sectional thickness. Alternatively the cross-sectional thickness may be in a range of about 0.030 to about 0.075 mm, for example: about 0.030 to about 0.065 mm; about 0.050 to about 0.065 mm; or about 0.060 mm to about 0.075 mm. The cross-sectional thickness may be less than about 0.075 mm and equal to, equal to about, at least, or at least about: 0.050, 0.055, 0.060, 0.060, 0.065, or 0.070 mm. In another embodiment, the cross-sectional thickness is less than, or less than about: 0.075, 0.070, 0.065, 0.060, 0.055, 0.050, 0.045, 0.040, 0.035, or 0.030 mm. In yet another embodiment, the mean cross-sectional thickness is about, is less than, or less than about: 0.075, 0.070, 0.065, 0.060, 0.055, 0.050, 0.045, 0.040, 0.035, or 0.030 mm.

Rare earth catalysts include those catalysts that contain one or more rare earth metals, which include: scandium (Sc), yttrium (Y), lanthanum (La), cerium (Ce), praseodymium (Pr), neodymium (Nd), promethium (Pm), samarium (Sm), europium (Eu) gadolinium (Gd), terbium (Tb), dysprosium (Dy), holmium (Ho), erbium (Er), thulim (Tm), ytterbium (Yb), and lutetium (Lu). A neodymium-based catalyst is preferably used in one or more embodiments. Exemplary rare-earth catalysts include, but are not limited to: lanthanum trichloride ($LaCl_3$) and neodymium trichloride ($NdCl_3$). The catalyst could be a $Ln(AlMe_4)_3$ catalyst, wherein Ln can be, for example, La, Ce, Pr, Nd, Gd or Y. Residual rare earth content of polymeric articles according to one or more embodiments is in a range of greater than or equal to 0.1 mg/kg and less than or equal to 100 mg/kg, and all values and subranges there between.

In one embodiment the residual rare earth content in a polymeric article is equal to, equal to about, less than, or less than about: 100 mg/kg, 90 mg/kg, 80 mg/kg, 70 mg/kg, 60 mg/kg, 50 mg/kg, 40 mg/kg, 30 mg/kg, 20 mg/kg, 10 mg/kg, 5 mg/kg, 2 mg/kg, 1 mg/kg, 0.5 mg/kg, 0.4 mg/kg, 0.3 mg/kg, 0.2 mg/kg, or 0.1 mg/kg. In another embodiment the residual rare earth content in a polymeric article is equal to, equal to about, greater than, or greater than about: 0.1 mg/kg, 0.2 mg/kg, 0.3 mg/kg, 0.4 mg/kg, 0.5 mg/kg, 1 mg/kg, 2 mg/kg, 5 mg/kg, 10 mg/kg, 20 mg/kg, 30 mg/kg, 40 mg/kg, 50 mg/kg, 60 mg/kg, 70 mg/kg, 80 mg/kg, 90 mg/kg, or 100 mg/kg. In yet another embodiment, the residual rare earth content in a polymeric article is in a range between any of these recited values.

Embodiments of the disclosure further comprise condoms. Embodiments further comprise condoms that are formed without using coagulants. Embodiments comprise a condom that includes an open end, a closed end, and a tubular sheath extending from the closed end to the open end. FIG. 1 is a perspective schematic view of a condom according to an embodiment. A rare earth catalysed polyisoprene (PI) condom 100 disclosed herein comprises a closed end 104 and an open end 108. A tubular shaft 106 extends from the closed end 104 to the open end 108, which has an opening 110 opposite a teat end 102 of the closed end 104. Optionally, the condom further comprises a bead 114. The tubular shaft of the condom comprises the rare earth catalysed PI particles, which may be provided by an aqueous rare earth catalysed PI latex composition. The aqueous latex compositions may have a solids content in the range of about 55% to about 68% by weight, or about 55% to about 60% by weight; for example in an amount of, about, at least, or at least about: 55%, 56%, 57%, 58%, 59%, 60%, 61%, 62%, 63%, 64%, 65%, 66%, 67%, or 68%, by weight. The compositions may further comprise additional water, preferably deionised water, to result in a composition solids content in the range of 50% to 55% by weight. Optionally, the aqueous latex compositions may further comprise one or more thickeners (for example a cellulose such as hydroxyethyl cellulose) and/or stabilisers/surfactants. In another embodiment, one or more heat sensitising agents may be used. Colourants and/or pigments may optionally be added to the aqueous latex compositions.

Methods

Disclosed herein is a method for producing synthetic polyisoprene articles comprises using emulsions of synthetic polyisoprene resins catalysed using rare earth catalysts. Generally, synthetic polyisoprene particles of rare earth catalysed polyisoprene material comprise of greater than or equal to 97.0% cis-1,4-polyisoprene by weight.

The synthetic polyisoprene particles may comprise a median particle diameter in the range of approximately from 0.2 to 2 micrometres. Preferably about 0.7 micrometres. In one embodiment the synthetic polyisoprene particles comprise a median particle diameter equal to, equal to about, at least, or at least about: 0.2, 0.3, 0.4, 0.5, 0.6, 0.7, 0.8, 0.9, 1, 1.1, 1.2, 1.3, 1.4, 1.5, 1.6, 1.7, 1.8, 1.9, or 2.0 micrometres. In one or more embodiments, the synthetic polyisoprene particles comprise a maximum median particle diameter of about 1 micrometre, or 1 micrometre. In another embodiment, the synthetic polyisoprene particles comprise a maximum median particle diameter equal to, or equal to about: 0.5, 0.6, 0.7, 0.8, 0.9, 1, 1.1, 1.2, 1.3, 1.4, 1.5, 1.6, 1.7, 1.8, 1.9, or 2.0 micrometres.

Herein, the method may further comprise a pre-vulcanization composition and post-vulcanization composition along with conventional emulsion additives, such as stabilisers, pH control agents, antioxidants, and preservatives, etc. A typical synthetic polyisoprene latex composition is provided in terms of 100 parts by weight of dry rubber (PHR). During compounding, the components of the latex composition may be suspended in water.

The pH of a rare earth catalysed synthetic polyisoprene material, for example a resin, may have a pH in a range of about 9.0 to about 12.0. In one embodiment, the pH is equal to, is about, is at least, or is at least about: 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4 or 12.5. In another embodiment, the pH is equal to, is about, is less than, or is less than about: 12.5, 12.4, 12.3, 12.2, 12.1, 12.0, 11.9, 11.8, 11.7, 11.6, 11.5, 11.4, 11.3, 11.2, 11.1, 11.0, 10.9, 10.8, 10.7, 10.6, 10.5, 10.4, 10.3, 10.2, 10.1, 10.0, 9.9, 9.8, 9.7, 9.6, 9.5, 9.4, 9.3, 9.2, 9.1 or 9.0. In yet another embodiment, the pH is in a range between any of these recited values.

In one embodiment, a pH adjustor may be used/present, for example ammonium hydroxide and/or potassium hydroxide. In another embodiment no pH adjustors are used/present. In another embodiment one or more pH adjustors may be present in an amount of greater than 0 but less or equal to about 5 PHR, for example in a range of great than 0 but equal to or about: 0.25 PHR, 0.50 PHR, 0.75 PHR, 1.00 PHR, 1.25 PHR, 1.50 PHR, 1.75 PHR, 2.00 PHR, 2.25 PHR, 2.50 PHR, 2.75 PHR, 3.00 PHR, 3.25 PHR, 3.50 PHR, 3.75 PHR, 4.00 PHR, 4.25 PHR, 4.50 PHR, 4.75 PHR, or 5.00 PHR. In yet another embodiment, the pH adjustor is present in a range between any of these recited values.

In general, a pre-vulcanizing composition may include sulfur in the range of 0.6 to 1.8 PHR, for example about 0.6 to about 1.2 PHR. In one embodiment, sulfur may be present in a pre-vulcanizing composition in an amount equal to, equal to about, at least or at least about: 0.6 PHR, 0.7 PHR, 0.8 PHR, 0.9 PHR, 1.0 PHR, 1.1 PHR, 1.2 PHR, 1.3 PHR, 1.4 PHR, 1.5 PHR, 1.6 PHR, 1.7 PHR, or 1.8 PHR. In another embodiment, sulfur may be present in a pre-vulcanizing composition in an amount equal to, equal to about, less than, or less than about: 1.8 PHR, 1.7 PHR, 1.6 PHR, 1.5 PHR, 1.4 PHR, 1.3 PHR, 1.2 PHR, 1.1 PHR, 1.0 PHR, 0.9 PHR, 0.8 PHR, 0.7 PHR, or 0.6 PHR. In yet another embodiment, sulfur may be present in a pre-vulcanizing composition in an amount in a range between any of these recited values.

Herein, an accelerator package may include zinc diethyldithiocarbamate (ZDEC) and/or zinc dibutyldithiocarbamate (ZDBC) accelerator, and/or sodium dibutyldithiocarbamate (SDBC) accelerator, a diisopropyl xanthogen polysulphide (DIXP) accelerator and/or a dipentamethylene thiuramtetrasulfide (DPTT) accelerator. The pre-vulcanizing composition may comprise a total accelerator content is in the range of 0.6 to 2.5 PHR. One or more accelerators may be present. In one embodiment, the total accelerator content in a pre-vulcanizing composition is in an amount equal to, equal to about, at least or at least about: 0.6 PHR, 0.7 PHR, 0.8 PHR, 0.9 PHR, 1.0 PHR, 1.1 PHR, 1.2 PHR, 1.3 PHR, 1.4 PHR, 1.5 PHR, 1.6 PHR, 1.7 PHR, 1.8 PHR, 1.9 PHR, 2.0 PHR, 2.1 PHR, 2.2 PHR, 2.3 PHR, 2.4 PHR, or 2.5 PHR. In another embodiment, the total accelerator content in a pre-vulcanizing composition is in an amount equal to, equal to about, less than, or less than about: 2.5 PHR, 2.4 PHR, 2.3 PHR, 2.2 PHR, 2.1 PHR, 2.0 PHR, 1.9 PHR, 1.8 PHR, 1.7 PHR, 1.6 PHR, 1.5 PHR, 1.4 PHR, 1.3 PHR, 1.2 PHR, 1.1 PHR, 1.0 PHR, 0.9 PHR, 0.8 PHR, 0.7 PHR, or 0.6 PHR. In yet another embodiment, the total accelerator content in a pre-vulcanizing composition is in an amount in a range between any of these recited values.

The pre-vulcanizing composition may comprise a zinc oxide activator.

The pre-vulcanizing composition may comprise one or more anti-oxidants and/or anti-ozonants. For example, one or more one or more anti-oxidants and/or anti-ozonants in a range of about 0.1 to 1.5 PHR, for example equal to, equal to about, at least, or at least about: 0.1 PHR, 0.2 PHR, 0.3 PHR, 0.4 PHR, 0.5 PHR, 0.6 PHR, 0.7 PHR, 0.8 PHR, 0.9 PHR, 1 PHR, 1.1 PHR, 1.2 PHR, 1.3 PHR, 1.4 PHR, or 1.5 PHR.

The pre-vulcanization composition may comprise a surfactant. The surfactants may include one or more anionic surface active agents (e.g., a carboxylate, sulphonates, and/or sulphates) and/or non-ionic surface active agents. The surfactant may be a salt of a fatty acid, such as sodium stearate, sodium oleate, or potassium caprylate. Some embodiments comprise more than one surfactant, e.g., potassium caprylate, also known as potassium salt of octanic acid and sodium dodecyl benzene sulphonate (SDBS). Exemplary embodiments comprise a surfactant package having potassium caprylate, sodium dodecyl benzene sulphonate (SDBS) and polyoxyethylene cetyl/stearyl ether in the range of 0.3 to approximately 1.5 PHR. An anti-oxidant and preservative package includes a butylated reaction product of p-cresol and, optionally, dicyclopentadiene in the range of 0.3 to approximately 1.0 PHR. One or more surfactants may be present. In one embodiment, one or more surfactants are present in a range of about 0.3 PHR to about 3.0 PHR, for example about 0.8 PHR to about 1.0 PHR. In one embodiment, the total surfactant content in a pre-vulcanizing composition is in an amount equal to, equal to about, at least or at least about: 0.3 PHR, 0.4 PHR, 0.5 PHR, 0.6 PHR, 0.7 PHR, 0.8 PHR, 0.9 PHR, 1.0 PHR, 1.1 PHR, 1.2 PHR, 1.3 PHR, 1.4 PHR, 1.5 PHR, 1.6 PHR, 1.7 PHR, 1.8 PHR, 1.9 PHR, 2.0 PHR, 2.1 PHR, 2.2 PHR, 2.3 PHR, 2.4 PHR, 2.5 PHR, 2.6 PHR, 2.7 PHR, 2.8 PHR, 2.9 PHR, or 3.0 PHR. In another embodiment, the total surfactant content in a pre-vulcanizing composition is in an amount equal to, equal to about, less than, or less than about: 3.0 PHR, 2.9 PHR, 2.8 PHR, 2.7 PHR, 2.6 PHR, 2.5 PHR, 2.4 PHR, 2.3 PHR, 2.2 PHR, 2.1 PHR, 2.0 PHR, 1.9 PHR, 1.8 PHR, 1.7 PHR, 1.6 PHR. 1.5 PHR, 1.4 PHR, 1.3 PHR, 1.2 PHR, 1.1 PHR, 1.0 PHR, 0.9 PHR, 0.8 PHR, 0.7 PHR, 0.6 PHR, 0.5 PHR, 0.4 PHR, or 0.3 PHR. In yet another embodiment, the total surfactant content in a pre-vulcanizing composition is in an amount in a range between any of these recited values.

The sulfur in the pre-vulcanizing package is, for example, elemental sulfur having a high soluble sulfur content, typically of the $S_8$ ring structure. The pre-vulcanization composition further comprises an accelerator. For example, an accelerator that can break or disrupt the $S_8$ sulfur ring structure is zinc dithiocarbamate. Reference to "high soluble sulfur content" means having enough soluble sulfur present to form sufficient to permeate into latex particles in the aqueous latex emulsion and crosslink during curing to achieve commercially acceptable articles, such as condoms and/or gloves. The pre-vulcanization of the synthetic latex particles in the latex occurs over a period of time at a chosen temperature to a desired degree of pre-vulcanization. The degree of pre-vulcanization at different points after initial compounding of the synthetic latex particles may be monitored by at least one of four tests. An equilibrium-swelling test, which uses any suitable solvent, measures the equilibrium swelling of films dried down from the synthetic latex. A relaxed modulus test gauges the vulcanization of the relaxed modulus at 100% extension (MR100) of films dried down from the dissolved latex. Similarly, a pre-vulcanized relaxed modulus test (PRM) measures the relaxed modulus at 100% extension of the pre-vulcanized films.

A Toluene Swell Index (TSI) test may be used to measure the level of crosslinking by immersing the dried casted film sample in the toluene and calculate the swollen rate. Cast film of the compounded latex to produce film thickness of 0.10-0.15 mm and dry the film at 50+/−3° C. for 10 minutes and/or leave the film at ambient temperature until it is fully dried. Peel off the film with the powder such as corn starch or calcium carbonate ($CaCO_3$) to prevent the film surface being stick to itself. Cut a disc sample with a die cutter. Submerge the disc film into the toluene for 60 minutes. Measure the diameter of the swollen film. Calculate the % swollen by subtract the original disc diameter from the swollen film diameter and divided by the original film diameter. The latex particles progress from a non-crosslink stage (index >220%), to a partial crosslink stage (index <220%), then to a semi-crosslink stage (index <180%) and finally to a fully crosslink stage (index <100%) as pre-vulcanizing sulfur is incorporated within the particle.

Compounding methods according to embodiments of the disclosure include the mixing the latex together with chemical additives and stirring periodically and examining for permeation of pre-vulcanization agents into the synthetic polyisoprene particles for example, by using an isopropanol index test. Polyisoprene latex has an inherent tendency to flock and 'case harden' due to a peripheral reaction with sulfur catalysed by ZDBC or ZDEC, i.e., an outside surface hardens, preventing crosslinking of internal molecules. The presence of surfactants and creation of opened out $S_8$ chains of sulfur enables the diffusion of sulfur into the particles. In other words, the diffusion of sulfur into the particles, i.e., 'through-hardening' can occur, allowing the crosslinking of internal molecules. A latex article or product comprising a through-hardened structure is stronger than an otherwise similar latex article or product having a case-hardened structure.

The residual sulfur concentration may be measured by a process known in the art, for example test method UPB/P/004 by the Rubber Research Institute of Malaysia. The residual sulfur may be in a range of about 0.8 to about 1.5%. For example the residual sulfur may be present in an amount of, about, at least, or at least about: 0.8%, 0.9%, 1%, 1.1%, 1.2%, 1.3%, 1.4%, or 1.5%.

TSI may be substituted with an isopropanol index test, which is according to latex particles progressing from a very tacky feel (index ~1.0) to a lesser degree of tacky feel (index 3) as pre-vulcanizing sulfur is incorporated within the particle. In one or more embodiments, pre-vulcanization is acceptable once the isopropanol index is 3.

The pre-vulcanization composition provides sulfur to synthetic polyisoprene latex particles in the aqueous synthetic polyisoprene emulsion for pre-vulcanizing the intra-particle regions. During pre-vulcanization, the ring structure of the sulfur is broken by the catalytic action of the accelerator, e.g., zinc dithiocarbamate, which penetrates the polyisoprene particles and initially interacts with the isoprene double bonds therein.

Without intending to be bound by theory, it is believed that the penetration of the components of the pre-vulcanizing composition into the polyisoprene particles is a function of the diffusion process, which may be a linear function of time. The penetration of the components comprises an exponential function of temperature, reflecting a thermally activated process. Therefore, increasing the temperature by a few degrees during the pre-vulcanization step increases the pre-vulcanization rate. For example, pre-vulcanization at room temperature may be about 3-5 days or as much as about 9 days, while pre-vulcanization at, for e.g., about 50-70° C., may take about 3-7 hours. In the absence of pre-vulcanization of the synthetic polyisoprene particles, crosslinking predominantly occurs in the periphery (i.e., case-hardening) of the synthetic polyisoprene particles, resulting in weak particles. Attempts to crosslink the inter-particle region within the particles only during post-vulcanization, discussed below, results in over crosslinking of the intra-particle regions, which, in turn, results in a latex product with poor stretch properties.

The post-vulcanization composition includes amorphous or polysulfur, which is insoluble at latex emulsion temperature, e.g. 20-40° C., but is soluble at a vulcanization or cure temperature, e.g., 110-150° C. (such as about, or at least about: 110, 115, 120, 125, 130, 135, 140, 145, or 150° C., or any range there between). Generally, the post-vulcanization composition comprises accelerators such as, but not limited to, zinc diethyldithiocarbamate (ZDEC), zinc dibutyldithiocarbamate (ZDBC), sodium diethyldithiocarbamate (SDEC), sodium dibutyldithiocarbamate (SDBC), a thiuram compound and a xanthogen. Examples of suitable xanthogens include, but are not limited to, diisopropyl xanthogen polysulphide (DIXP), diisopropyl xanthogen, tetraethylthiuram disulfide, and xanthogen sulfide. DIXP is a suitable xanthogen owing to its polysulphidic donor properties. The post-vulcanization composition may further comprise a thiuram accelerator. An example of a polysulphidic thiuram accelerator is dipentamethylene thiuramtetrasulfide (DPTT).

Another example of a thiuram compound is tetrabenzyl thiuram disulfide. Zinc oxide may also be added as an activator.

The post-vulcanization composition provides the ability to crosslink regions between the particles of synthetic polyisoprene or inter-particle regions thereby assuring a high quality substantially uniformly cured synthetic polyisoprene product.

The post-vulcanization composition activates inter-particle cross-linking at a temperature of, e.g., 100-150° C. (such as about, or at least about: 100, 105, 110, 115, 120, 125, 130, 135, 140, 145, or 150° C., or any range there between). In addition, post-vulcanization processes also crosslink the synthetic polyisoprene particles with sulfur. Such post-vulcanization results in a more homogeneous latex coating having greater strength and elongation properties. The composition produced can be stable for up to approximately 5 days at 20° C. to 25° C. and is useful for a production line.

Table 1 shows an exemplary embodiment of a rare earth (RE) catalysed synthetic polyisoprene resin latex composition for producing a polymeric article. The latex composition is preferably aqueous.

TABLE 1

| Formulation - RE Catalysed | |
| --- | --- |
| Component | Quantity Per Hundred Dry Rubber (PHR) |
| Synthetic Polyisoprene Resin RE catalysed (e.g., see Tables 2 and 3) | 100 |
| Polyoxyethylene cetyl-stearyl ether | 0.15-0.35 |
| Octanoic acid; Potassium salt | 0.15-0.35 |
| Sodium dodecyl benzene sulfonate | 0.15-0.35 |
| Ammonium hydroxide | 0.00-0.30 |
| Sulphur | 0.60-1.20 |
| Zinc oxide | 0.05-0.5 |
| ZDEC/ZDBC | 0.30-0.80 |
| SDBC/SDEC | 0.10-0.50 |
| DXP/Diisopropyl Xanthogen/Xanthogen Sulfide | 0.30-0.80 |
| Butylated reaction product of p-cresol & dicyclopentadiene | 0.30-1.00 |

A typical mixing sequence of an aqueous synthetic latex emulsion according to Table 1 is:

Phase I: 3-5 days at 20-30° C. Addition of chemicals for pre-vulcanization including: sulfur, ZDEC/ZDBC, surfactant package with potassium caprylate and polyoxyethylene cetyl/stearyl ether.

Phase II: prior to dip. Addition of post-vulcanization sulfur source and accelerators including DXP, SDBC, SDEC, tetrabenzyl thiuram disulfide and surfactants when TSI index <100%.

Table 2 shows an exemplary embodiment of properties of a rare earth (RE) catalysed synthetic polyisoprene resin latex composition for producing a polymeric article.

TABLE 2

| Properties of RE Catalysed Synthetic PI | |
| --- | --- |
| Appearance | Milky white liquid |
| Total solid content (%) | 55.0-60.0 |
| Viscosity (mPa · s) | 100-150 |
| pH (at 25° C.) | 9.5-12.0 |

Table 3 shows a comparison of pre-vulcanization behaviour of an exemplary anionic polyisoprene and an exemplary Ziegler-Natta catalysed synthetic polyisoprene resin and an exemplary rare earth catalysed synthetic polyisoprene resin.

TABLE 3

| | PI Resin | | |
| --- | --- | --- | --- |
| Polymerisation | Anionic IR | Ziegler-Natta (ZN) | Rare Earth (RE) |
| Microstructure | | | |
| Median particle size (μm) | Max 1.8 | Max 1.5 | About 0.7 |
| Cis-1,4 (% wt) | 92 | 96-97 | >97.0 |
| Trans-1,4 (% wt) | 1.50 | 0.50 | — |
| 3,4-isomers (% wt) | 6.50 | 2.5-3.5 | — |
| Macrostructure | Linear | Branched | Linear |
| Molecular weight distribution | Narrow | Narrow | Narrow |
| Average molecular weight (*$10^6$ g/mol) | 2-3 | 1 | 1.2 |
| Gel (% wt) | Intrinsically nil | 10.0-20.0 | Intrinsically nil |
| Ash (% wt) | 0.05-0.1 | 0.15-3.0 | — |
| Trace metal content (ppm) | 70 | 400-3000 | — |
| Stabilizer content (% wt) | 0.05-0.3 | 1 | <1 |
| TSC (%) | 63 | 60-64 | 55-60 |
| Viscosity (cps) | 150 | 50-150 | 100-150 |
| pH | 9.5-12.0 | 10.0-12.0 | 9.5-12.0 |
| Specific gravity g/cm³ | 0.91 | 0.91 | 0.94 |
| Colour | Amber 1500 | Light yellow | Milky white liquid |
| Residual solvent (ppm) | (0.15%) | 1000 (0.10%) | — |

The present disclosure further provides a method of forming a synthetic polyisoprene polymeric article. The method comprises disposing an elastomeric coating of a rare earth catalysed polyisoprene material on a former and curing the elastomeric coating to form an elastomeric layer of the polymeric article. The disposing step may comprise dipping a coagulant-free or coagulant coated former in an emulsion of the rare earth catalysed polyisoprene material, which may be an aqueous latex composition according to Table 1 having pre-vulcanized particles, at least once to form a thin layer of latex or elastomeric coating with individual particles of pre-vulcanized synthetic polyisoprene on the surface of the former. The former can be any suitable former as is known in the art. The present inventive composition is particularly useful for layering onto formers for condoms.

Embodiments of the rare earth catalysed formulations disclosed in Table 1, which may use RE PI resin of Tables 2-3, as well as other RE catalysed formulations, are capable of making condoms that comprise a greater amount of cis character, e.g., cis-1,4 isomer, of the polyisoprene molecules than the anionic catalysed polyisoprene and the Ziegler-Natta catalysed polyisoprene, improving the strength properties of products made with synthetic rare earth catalysed polyisoprene.

Also, the exemplary rare earth catalysed formulation of Table 1 has potentially lower total solids content, allowing the manufacture of thinner condoms (for example with a thickness in a range of about 0.030 mm to about 0.065 mm, such as about 0.050 mm to about 0.065 mm). And, the exemplary rare earth catalysed formulation of Table 1 has potentially lower viscosities (for example between about 30 to about 40 cps), during the dipping processes, allowing thinner condoms to be produced therefrom. Lower viscosities also allow a faster line speed during manufacturing.

Furthermore, the rare earth catalysed formulation of Table 1 produces smaller particle sizes, which allows a thinner film and improve sensitivity during use. Smaller particles also exhibit improved crosslinking, which improves the processability of thinner products. For example, preventing the condom or glove collapse during washing processes and allows powder to coat evenly on both inside and outside and, therefore, reducing defects.

Table 4 lists a typical dipping method for producing a condom using a rare earth catalysed polyisoprene resin that is pre-vulcanized, as described above in Table 1.

TABLE 4

| Process | Time | Temperature (° C.) |
| --- | --- | --- |
| Pre-vulcanization of polyisoprene latex | 3-5 days | 20-30 |
| Post-vulcanization and First dip (thickness of coating may be controlled by latex viscosity, TSC and former speed in dip tank) | — | — |
| Drying of latex coating | 1-3 minutes | 70-90 |
| Second dip (optional) | — | — |
| Drying of latex coating | 1-3 minutes | 50-100 |
| Beading/ring formation on the open end of the condom | — | — |
| Condom curing | 11-15 minutes | 125-135 |
| Leaching | 1-2 minutes | 75-90 |
| Stripping of the condoms from the former | — | — |

The method of dipping for the condoms using the surfactant-stabilised, pre-vulcanized synthetic polyisoprene latex composition is typically within the 5-day period, e.g., an average lifetime of synthetic polyisoprene latex emulsion tank. A condom former is dipped in the composition in a first dip. The wall thickness of the latex coating is controlled by the viscosity of latex, which is a function of the total solids content of the composition in the dip tank. The speed of movement of the formers while dipping also affects the wall thickness. The latex coating that coats the formers is dried at approximately 60-100° C. for approximately 1-3 minutes. The latex coating on the former is, optionally, dipped again into the composition to apply a second dip coating. The latex coating after the second dip is dried at approximately 60-80° C. for approximately 1-3 minutes. The open end of the condom is rolled to create a bead ring, which is distal to a tip of a closed end of the condom.

The coating can be post-vulcanized by heating the coating, e.g., to about 110 to 150° C. for approximately 8 to 15 minutes, to form an elastomeric layer of a condom. Exemplary embodiments include post-vulcanization that is achieved by heating in an oven at approximately 120° C. for approximately 12 minutes. During this period, the inter-particle regions are cross-linked. The intra-particle regions also undergo further crosslinking, producing a more homogeneous latex product. The condom is optionally leached in water at approximately 70-80° C. for about 1-2 minutes to remove residual surfactants and cross-linking agents from the condom. The condom is then stripped from the former. The latex articles, such as condoms, produced display higher strength and improved stretch, even when a low stereo-regularity synthetic polyisoprene is used. The synthetic polyisoprene articles are free from irritation-causing proteins that cause latex sensitivity issues.

Embodiments according to the disclosure comprise the use of a coagulant solution to wet the former and may include an exemplary aqueous solution of 5% calcium nitrate, although other concentrations are possible as are known to those in the art, such as an aqueous solution ranging in concentration from 6-40% calcium nitrate. Other salts, such as calcium chloride, calcium citrate, aluminium sulfate, and the like and/or mixtures thereof may be used. Furthermore, the coagulant solution may be aqueous, alcoholic, or a mixture of aqueous and alcoholic solutions/solvents. Weaker acid solutions may also be used as coagulants, such as formic acid, acetic acid, and other low pKa acids (for example an acid with a pKa in a range of about 3 to about 7), as are known to those in the art.

Embodiments according to the disclosure comprise the use of pre-vulcanizing and post-vulcanizing methods, the technology of which is disclosed in commonly-assigned U.S. Pat. Nos. 8,087,412; 8,464,719; 9,725,539; and 10,538, 609 which are incorporated by reference in entirety. Methods for determining the molecular weight between cross-links ($M_c$) are disclosed in U.S. Pat. Nos. 8,087,412; 8,464, 719; 9,725,539; and 10,538,609.

In one embodiment the $M_c$ of: a latex formulation following pre-vulcanization and/or post-vulcanization; or an article comprising or composed of the latex formulation, such a personal protective device, for example a condom, is less than, or less than about: 10750, 10500, 10250, 10000, 9750, 9500, 9250, 9000, 8800, 8600, 8400, 8200, 8000, 7800, 7600, 7400, 7200, 7000, 6900, 6800, 6700, 6600, or 6550 g/mol. In one embodiment the $M_c$ is less than about 6540 g/mol.

EXAMPLES

Example 1

Condoms according to formulation of Table 1 were produced. Tables 5-1, 5-2 and 5-3 show exemplary properties of the condoms herein produced using the rare earth catalysed polyisoprene resin.

TABLE 5-1

| Properties Condoms made of RE Catalysed Synthetic PI (non-lubricated unaged) | |
| --- | --- |
| Formulation | Table 1 |
| Thickness, mm[A] | Target thickness: 0.060-0.075 |
| | Average actual: 0.074 |
| Burst pressure, kPa[A] | 0.96-1.45 |
| Burst volume, L[A] | 34.2-50.7 |
| Force at Break, N[A] | 48.5-100.9 |
| Tensile strength, kPa[A] | 14.7-29.2 |
| Elongation at break, %[A] | 779-883 |
| Cis-1,4 (% wt)[B] | 99.0 |
| Nd rare earth residual (mg/kg)[C] | 85.4 ± 13.7 |

*Vulcanized at 120° C. for 10 minutes at TSI of 130.34%

TABLE 5-2

| Properties Condoms made of RE Catalysed Synthetic PI (non-lubricated unaged) | |
| --- | --- |
| Formulation | Table 1 |
| Thickness, mm[A] | Target thickness: 0.050-0.065 |
| | Average actual: 0.058 |
| Burst pressure, kPa[A] | 1.31-1.42 |
| Burst volume, L[A] | 42.5-46.0 |

*Vulcanized at 110° C. for 10 minutes at TSI of 130.34%

TABLE 5-3

| Properties Condoms made of RE Catalysed Synthetic PI (Silicone lubricated, Aged 7 days at 70° C.) | |
| --- | --- |
| Formulation | Table 1 |
| Thickness, mm[A] | Target thickness: 0.060-0.075 |
| | Average actual: 0.072 |
| Burst pressure, kPa[A] | 0.91-1.47 |
| Burst volume, L[A] | 25.1-37.3 |

*Vulcanized at 120° C. for 10 minutes at TSI of 130.34%

A Testing in accordance with ISO 23409:2011, ISO4074: 2015, and ASTM D3492-16.

B Both ATR and Pyrolysis FFIR were used. This was then followed by $^{13}$C NMR analysis to specifically look for the level of cis isomers and for any evidence of trans or 3,4 isomers. $^{13}$C NMR analysis was carried out on some solvent swollen strips in d-chloroform with 30 degree pulse, 3 second pulse delay and 40,000 pulses. The $^{13}$C NMR spectrum showed only peaks related to cis 1,4 polyisoprene.

C Uncoated condom. The elemental analysis was carried out according to SS EN ISO 17294-1:2004, ISO 17294-2:2016 (modified) and US EPA Method 200.8 Revision 5.4, 1994 (modified), modified to utilize a ICP-MS with mass spectrometer (ICP-SFMS).

A method of measuring molecular weight distribution and calculating crosslink density requires cutting of disks from condom samples and swelling the disk samples in toluene until equilibrium. The disks were initially weighed and after swelling they are weighed again. The equilibrium volume fraction ($V_r$) of the swelled rubber was calculated using equation shown below. In this equation $P_r$ is the density of rubber (0.92 g/cm³), $P_s$ is the density of toluene (0.862 g/cm³), $W_r$ is the weight of rubber before swelling and $W_s$ is the weight of swelled rubber.

$$V_r = \frac{\dfrac{W_r}{P_r}}{\dfrac{W_r}{P_r} + \dfrac{W_s - W_r}{P_s}}.$$

The volume fraction was used in the Florey-Rehner equation shown below to calculate the crosslink density. In this equation n is the crosslink density, $V_s$ is the molar volume of toluene the swelling solvent which is 106.3 cm³/mol, $V_r$ is the volume fraction of the rubber phase in the swollen gel, and $\chi$ is the toluene-cis polyisoprene interaction parameter, which is 0.39.

$$n = \frac{-1}{V_s} \frac{\left[\ln(1 - V_r) + V_r + \chi V_r^2\right]}{\left[V_r^{\frac{1}{3}} - 0.5\, V_r\right]}.$$

The molecular weight between crosslinks was calculated by the following equation.

$$M_c = \frac{P_r}{n}.$$

Table 6 shown below reports measured molecular weight between crosslinks and corresponding crosslink density for several of synthetic polyisoprene condoms manufactured according the embodiments of the subject disclosure. The higher the molecular weight between crosslinks, the lower the crosslink density becomes.

The data presented indicates that the process of the present disclosure results in synthetic polyisoprene condoms that have very consistent molecular weight between cross-links, providing a condom having adequate mechanical properties. The molecular weight between crosslinks ($M_c$) for the condoms according to the present embodiments can be 6,540 g/mol. The crosslink density according to the present embodiments is 0.000141 mol/cm³, which is comparable to that of natural rubber, which has a crosslink density of 0.000159 mol/cm³.

TABLE 6

| Molecular Weight | |
| --- | --- |
| Average volume fraction ($V_r$) | 0.1966 |
| N, mol/cm³ | $1.41 \times 10^{-4}$ |
| $M_c$, Da (atomic mass unit) | 6,540 |

Figure 2A:
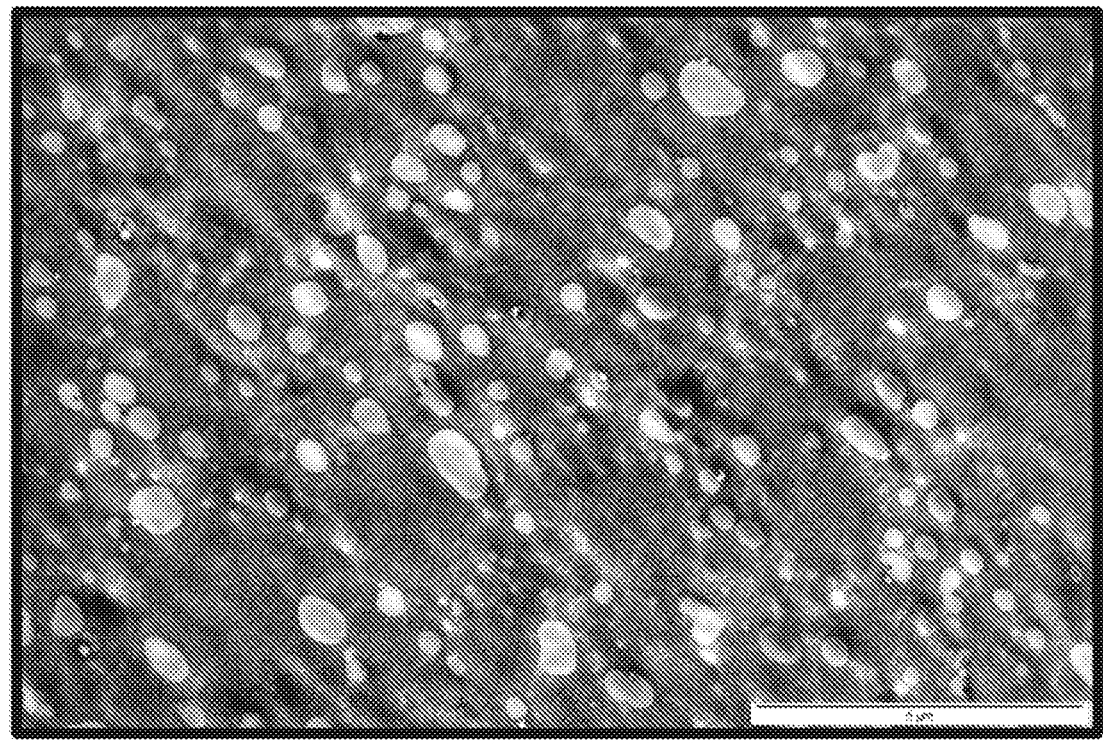
FIG. 2A is a first transmission electron microscopy (TEM) image.
Figure 2B:
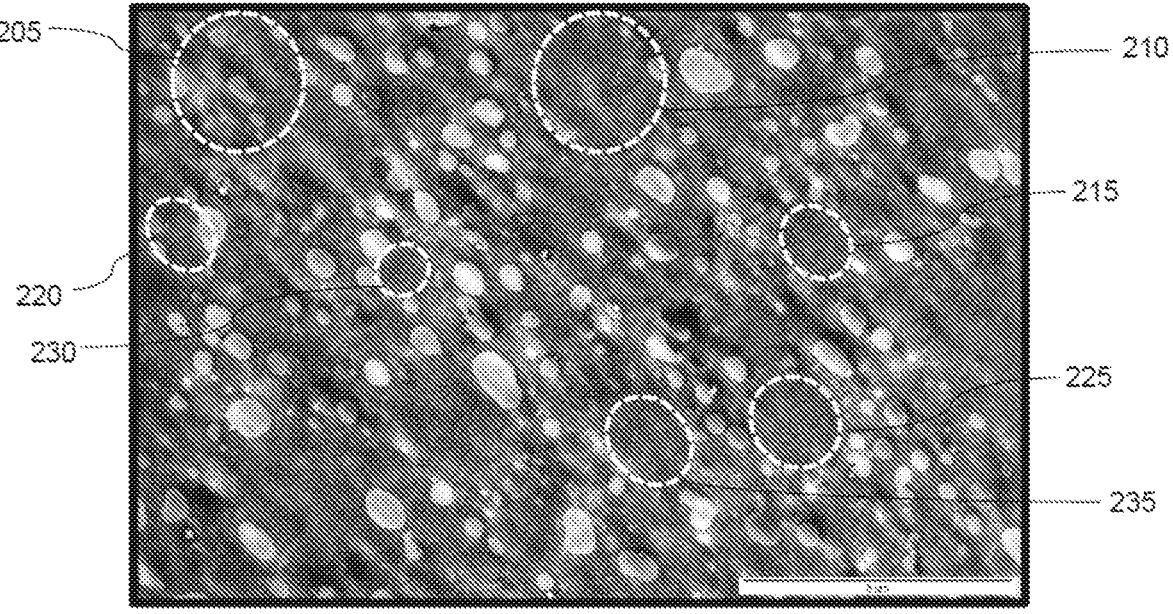
FIG. 2B is an annotated version of FIG. 2A, according to embodiments of the disclosure.
Figure 3:
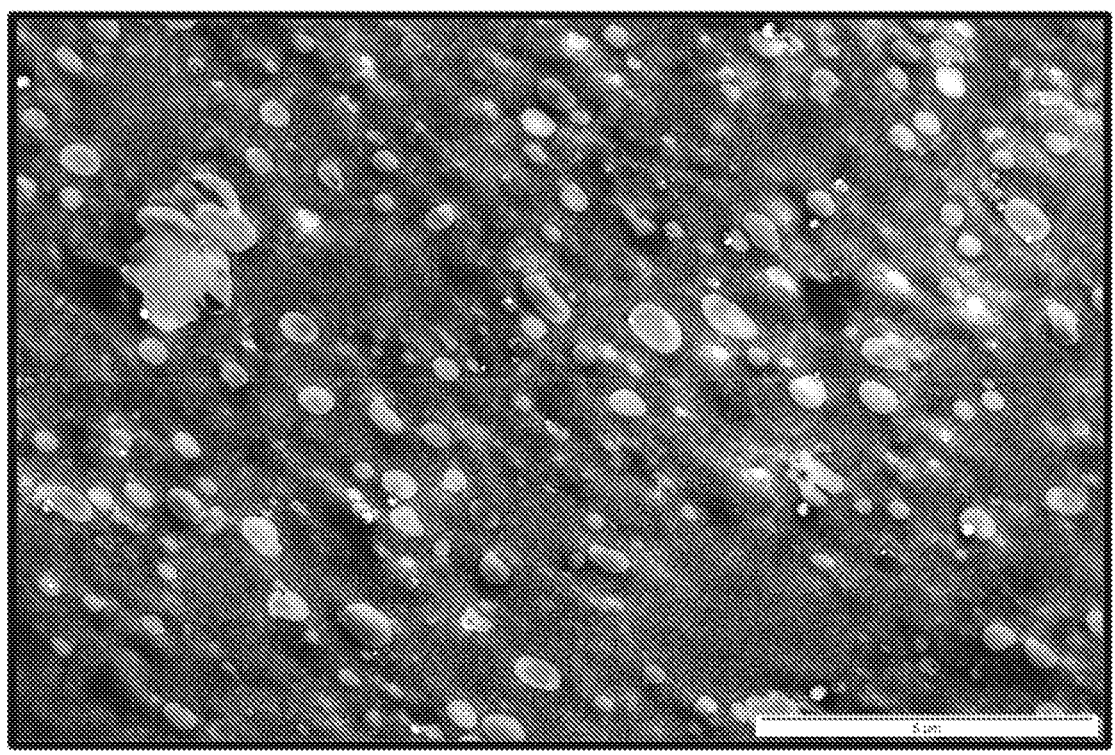
FIG. 3 depicts a second TEM image, according to embodiments of the disclosure.
Figure 4:
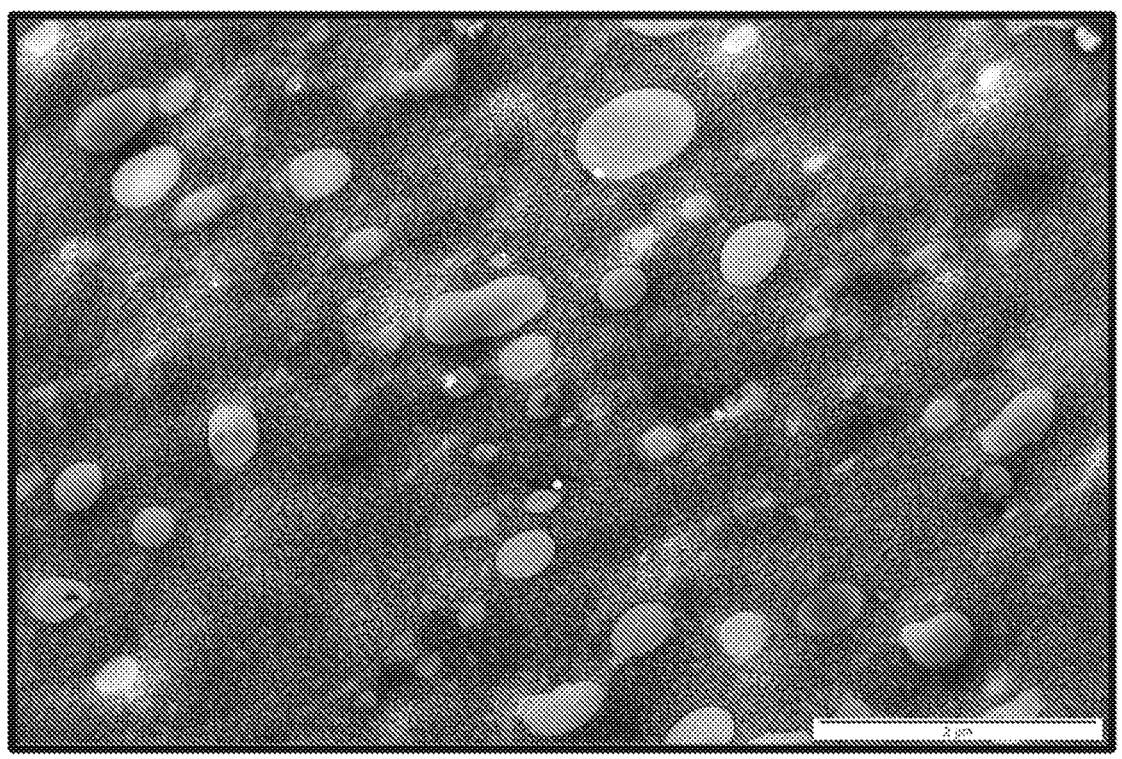
FIG. 4 depicts a third TEM image, according to embodiments of the disclosure.
Figure 5:
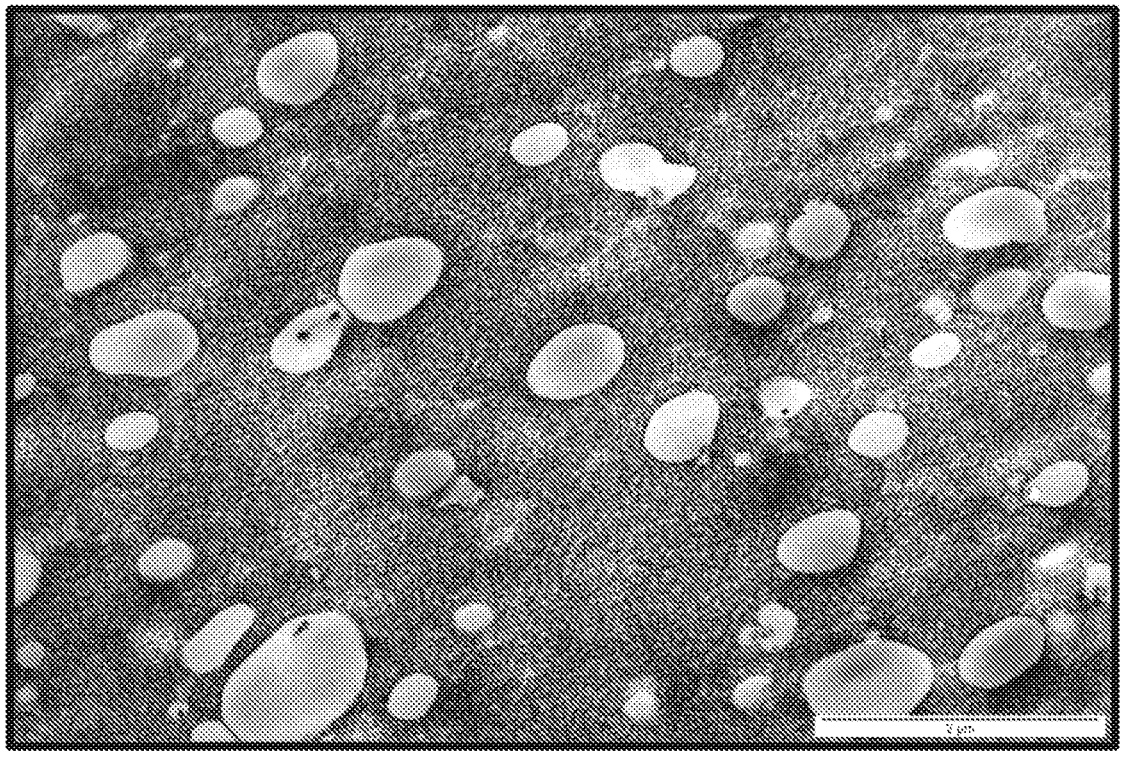
FIG. 5 depicts a fourth TEM image, according to embodiments of the disclosure.

FIG. 2A depicts a first transmission electron microscopy (TEM) image of a surface of a condom, and FIG. 2B is an annotated version of FIG. 2A, according to embodiments of the disclosure; FIG. 3 depicts a second TEM image of a surface of a condom, according to embodiments of the disclosure; FIG. 4 depicts a third TEM image of a surface of a condom, according to embodiments of the disclosure; FIG.

Figure 6:
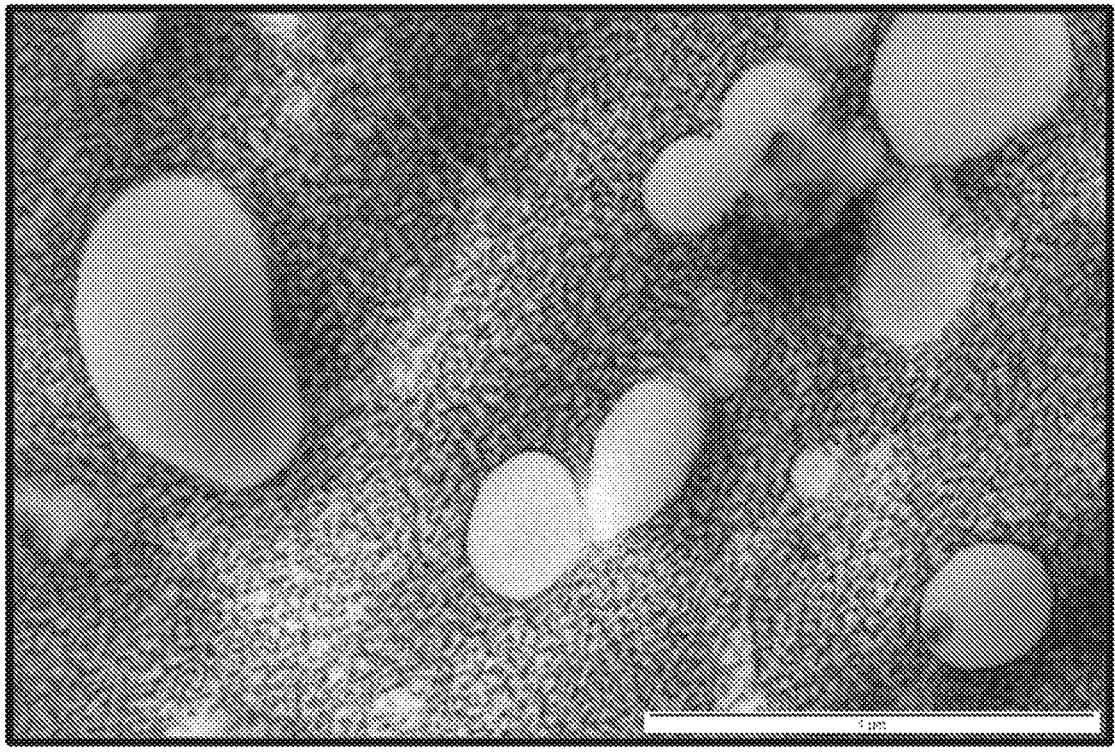
FIG. 6 depicts a fifth TEM image, according to embodiments of the disclosure.
Figure 7A:
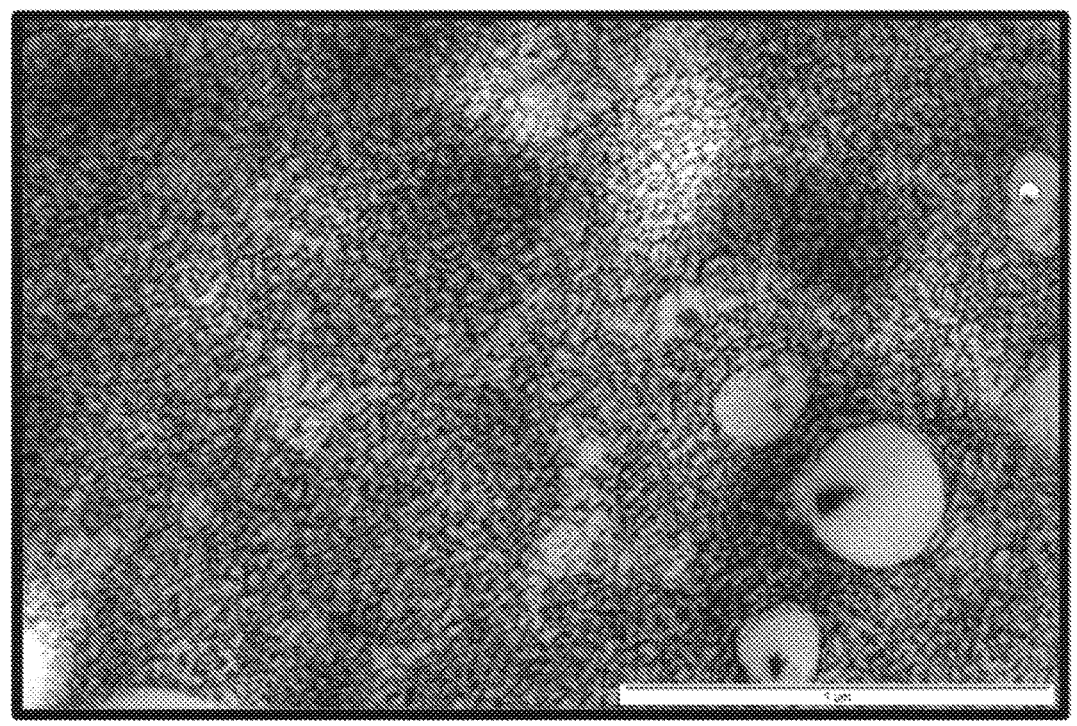
FIG. 7A depicts a sixth TEM image.
Figure 7B:
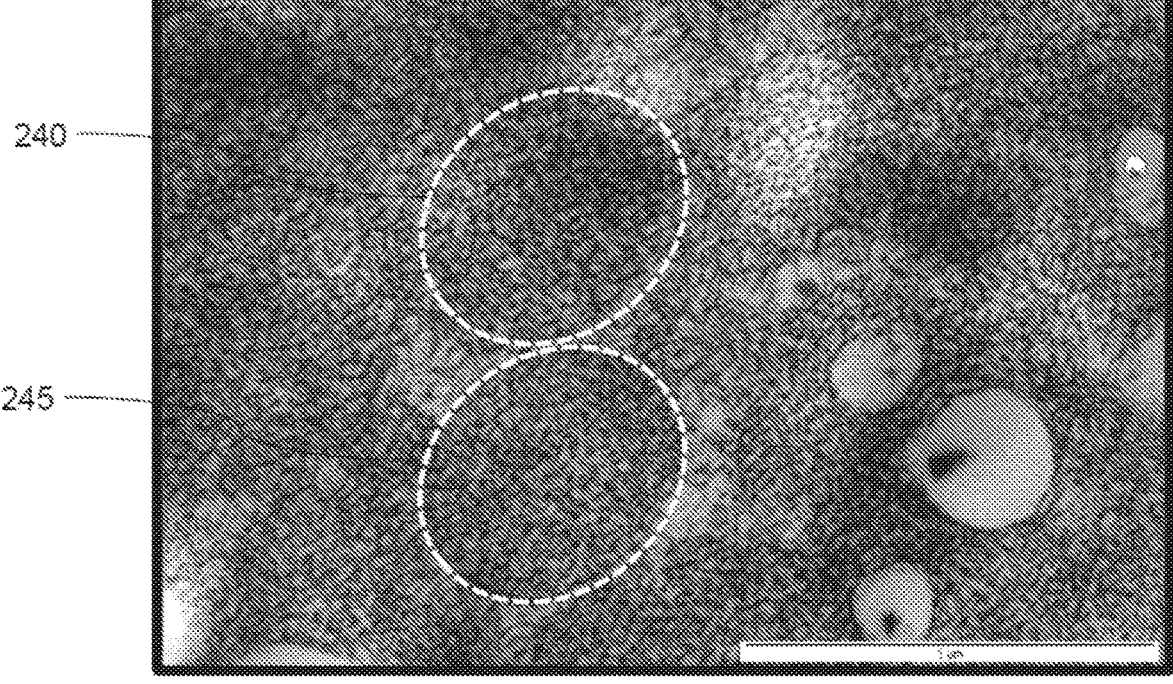
FIG. 7B is an annotated version of FIG. 7A, according to embodiments of the disclosure.

5 depicts a fourth TEM image of a surface of a condom, according to embodiments of the disclosure; FIG. 6 depicts a fifth TEM image of a surface of a condom, according to embodiments of the disclosure; and FIG. 7A depicts a sixth TEM image of a surface of a condom, and FIG. 7B is an annotated version of FIG. 7A, according to embodiments of the disclosure.

The condoms studied in the TEM images of FIGS. 2A, 3, 4, 5, 6, and 7A were prepared as follows. Each condom was washed in propan-2-ol to remove the lubricant and then dipped in propan-2-ol containing a small amount of talc to prevent adhesion and thus also facilitate handling. The condom was then air-dried. A number of rings were cut from the condom using a parallel, twin-blade cutter with the blades a nominal 10 mm apart. These rings were to be used for the two methods of analysis: network visualization by TEM and $V_r$ measurement by equilibrium swelling.

For the network visualisation, pieces of the condoms were first extracted overnight using hot acetone in a Soxhlet extractor. The samples were then dried prior to being swollen to equilibrium in styrene solution containing 1 wt % benzoyl peroxide initiator and 2 wt % dibutylphthalate plasticiser to aid sectioning. The swollen films were then placed in capsules with excess styrene solution and heated at 50-55° C. until the styrene had fully polymerised and become hard enough to produce good sections.

Ultra-thin sections of the samples were prepared by ultramicrotomy at room temperature using a diamond knife. The sections were collected on a water-filled trough and then relaxed with xylene vapour before collecting on TEM grids. All of the sections were then stained with osmium tetroxide vapour for 7 minutes. Osmium tetroxide reacts with carbon-carbon double bonds and therefore it increases the electron density of polymers containing unsaturated groups. Thus, it makes unsaturated polymers such as polyisoprene appear dark in the TEM relative to the polystyrene.

The rubber inside the latex particles is cross-linked and has therefore produced a styrene swollen rubber network. Rubber network is visible inside the latex particles and also between the latex particles. The rubber latex particles have diffuse boundaries but can be identified. This indicates that there is a tendency to resist the separation of the latex particles caused by the styrene-swelling in these areas. There are also polystyrene "voids"; areas where the rubber network is weak and styrene has infiltrated the structure. Some of the voids contain small dark particles of a more electron dense material. In the voids observed without particles it may be that a particle was above or below the plane of the micrographed section.

The uncertainty on the scale bar dimension is ±10% in all of the TEM micrographs.

FIG. 2B, which has a scale of 5 micrometres (μm) as annotated by shapes 205, 210, 215, 220, 225, 230, and 235, shows the outlines of PI particles. The cross-linking is substantially uniform throughout the thickness.

FIG. 7B, which has a scale of 1 micrometres (μm) as annotated by shapes 240 and 245, shows the outlines of PI particles. The cross-linking is substantially uniform throughout the thickness.

Example Embodiments

The present disclosure may rely on one or more of the following example embodiments.

Embodiment (a). A polymeric article comprising: an elastomeric layer comprising pre-vulcanized cured synthetic polyisoprene particles that comprise: a plurality of sulfur crosslinks and a rare earth catalysed polyisoprene material comprising a cis-1,4 isomer content of greater than 97.0% by weight and a rare earth element content of greater than or equal to 0.1 mg/kg and less than or equal to 100 mg/kg; wherein the synthetic polyisoprene particles are pre-vulcanized.

Embodiment (b). The polymeric article of embodiment (a), wherein the rare earth catalysed polyisoprene material comprises a cis-1,4 isomer content: greater than or equal to 97.75% by weight, greater than or equal to 97.50% by weight, greater than or equal to 98.00% by weight, greater than or equal to 98.25% by weight, greater than or equal to 98.50% by weight, greater than or equal to 98.75% by weight, greater than or equal to 99.00% by weight, or greater than or equal to 99.25% by weight.

Embodiment (c). The polymeric article of one of embodiments (a) to (b), wherein the cis-1,4 isomer content is about or greater than about 99.5% by weight.

Embodiment (d). The polymeric article of one of embodiments (a) to (c), wherein the rare earth catalysed polyisoprene material comprises a trans-1,4 isomer content of 0.50% by weight or less, optionally a trans-1,4 isomer content of about, less than, or less than about: 0.50, 0.45, 0.40, 0.35, 0.30, 0.25, 0.20, 0.15 or 0.10% by weight.

Embodiment (e). The polymeric article of one of embodiments (a) to (d), wherein the rare earth catalysed polyisoprene material comprises a 3,4 isomer content of 3.00% by weight or less, optionally a 3,4 isomer content of about, less than, or less than about: 3.00, 2.75. 2.50, 2.25, 2.00, 1.75, 1.50, 1.25, 1.00, 0.75 or 0.50% by weight.

Embodiment (f). The polymeric article of one of embodiments (a) to (e), wherein the article has a thickness: in a range of from about 0.050 to about 0.075 mm; in a range of from about 0.050 to about 0.065 mm; in a range of from about 0.060 to about 0.075 mm; in a range of about 0.030 to about 0.065; in a range of about 0.030 to about 0.075; or a thickness of about, or less than about: 0.075, 0.070, 0.065, 0.060, 0.055, or 0.050, 0.045, 0.040, 0.035, or 0.030 mm.

Embodiment (g). The polymeric article of one of embodiments (a) to (f), wherein the elastomeric layer comprises a post-vulcanized structure having a molecular weight between crosslinks (Me) of: less than, less than about: 10750, 10500, 10250, 10000, 9750, 9500, 9250, 9000, 8800, 8600, 8400, 8200, 8000, 7800, 7600, 7400, 7200, 7000, 6900, 6800, 6700, 6600, or 6550 g/mol; or less than, or less than about 6540 g/mol.

Embodiment (h). The polymeric article of one of embodiments (a) to (g), wherein the synthetic polyisoprene particles have a median or maximum median particle diameter equal to, equal to about, at least, or at least about: 0.2, 0.3, 0.4, 0.5, 0.6, 0.7, 0.8, 0.9, 1, 1.1, 1.2, 1.3, 1.4, 1.5, 1.6, 1.7, 1.8, 1.9, or 2.0 micrometres; or of approximately from 1 micrometre.

Embodiment (i1). The polymeric article of one of embodiments (a) to (h), wherein the synthetic polyisoprene particles are bonded to each other through intra-polyisoprene particle crosslinks and inter-polyisoprene particle crosslinks.

Embodiment (i2). The polymeric article of any one of embodiments (a) to (i2) wherein the polymeric article is personal protective equipment optionally selected from a gloves and a condom.

Embodiment (j). A condom comprising: an elastomeric layer comprising cured synthetic polyisoprene particles that are pre-vulcanized and comprise sulfur crosslinks; wherein the synthetic polyisoprene particles comprise a rare earth catalysed polyisoprene material that comprises: a cis-1,4 isomer content of greater than 97.0% by weight; a trans-1,4 isomer content of 1% by weight or less; and a 3,4 isomer content of 1% by weight or less.

Embodiment (k). The condom of embodiment (j), wherein the elastomeric layer forms an open end, a closed end, and a tubular sheath extending from the closed end to the open end.

Embodiment (l). The condom of one of embodiments (j) to (k), wherein the rare earth catalysed polyisoprene material comprises a branched macrostructure.

Embodiment (m). The condom of one of embodiments (j) to (l), wherein the elastomeric layer comprises a post-vulcanized structure having a molecular weight between crosslinks ($M_c$) of: less than, or less than about: 10750, 10500, 10250, 10000, 9750, 9500, 9250, 9000, 8800, 8600, 8400, 8200, 8000, 7800, 7600, 7400, 7200, 7000, 6900, 6800, 6700, 6600, or 6550 g/mol; or less than, or less than about 6,540 g/mol.

Embodiment (n). The condom of one of embodiments (j) to (m), wherein the synthetic polyisoprene particles have a median or maximum median particle diameter of: equal to, equal to about, at least, or at least about: 0.2, 0.3, 0.4, 0.5, 0.6, 0.7, 0.8, 0.9, 1, 1.1, 1.2, 1.3, 1.4, 1.5, 1.6, 1.7, 1.8, 1.9, or 2.0 micrometres; or approximately from 1 micrometre.

Embodiment (o). A method for producing a polymeric article, comprising: pre-vulcanizing an emulsion comprising a rare earth catalysed polyisoprene material comprising a cis-1,4 isomer content of greater than 97.0% by weight; disposing an elastomeric coating of the emulsion comprising the rare earth catalysed polyisoprene material on a former; and curing the elastomeric coating to form an elastomeric layer of the polymeric article; wherein the elastomeric layer comprises cured synthetic polyisoprene particles cross-linked by sulfur and a rare earth element content of greater than or equal to 0.1 mg/kg and less than or equal to 100 mg/kg.

Embodiment (p). The method of embodiment (o), wherein the polymeric article comprises a condom and the elastomeric layer forms an open end, a closed end, and a tubular sheath extending from the closed end to the open end.

Embodiment (q). The method of one of embodiments (o) to (p), wherein the cured synthetic polyisoprene particles comprise both intra-polyisoprene particle sulfur-crosslinks and inter-polyisoprene particle sulfur-crosslinks.

Embodiment (r). The method of one of embodiments (o) to (q), wherein a post-vulcanization composition is added to the emulsion before the emulsion is disposed on the former.

Embodiment (s). An article produced by the method of any one of embodiments (o) to (r).

Embodiment (t). The article of any one of embodiments (a) to (i2) or (s), wherein the article is a condom.

To facilitate understanding, identical reference numerals have been used, where possible, to designate comparable elements that are common to the figures. The figures are not drawn to scale and may be simplified for clarity. It is contemplated that elements and features of one embodiment may be beneficially incorporated in other embodiments without further recitation.

It is to be understood that various changes and modifications to the embodiments described herein will be apparent to those skilled in the art. Such changes and modifications can be made without departing from the spirit and scope of the present disclosure and without demising the attendant advantages. It is, therefore, intended that such changes and modifications be covered by the appended claims.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A method for producing a polymeric article, comprising:

pre-vulcanizing an emulsion comprising a rare earth catalysed polyisoprene material comprising a cis-1,4 isomer content of greater than 97.0% by weight; disposing an elastomeric coating of the emulsion comprising the rare earth catalysed polyisoprene material on a former; and curing the elastomeric coating to form an elastomeric layer of the polymeric article, wherein the elastomeric layer comprises cured synthetic polyisoprene particles cross-linked by sulfur and a rare earth element content of greater than or equal to 0.1 mg/kg and less than or equal to 100 mg/kg.

2. A polymeric article produced by a method according to claim 1.

3. The polymeric article of claim 2, wherein the polymeric article is a condom.

4. The method of claim 1, wherein the polymeric article comprises a condom and the elastomeric layer forms an open end, a closed end, and a tubular sheath extending from the closed end to the open end.

5. The method of claim 1, wherein the cured synthetic polyisoprene particles comprise both intra-polyisoprene particle sulfur-crosslinks and inter-polyisoprene particle sulfur-crosslinks.

6. The method of claim 1, wherein a post-vulcanization composition is added to the emulsion before the emulsion is disposed on the former.

7. A condom comprising:

an elastomeric layer comprising cured synthetic polyisoprene particles that are pre-vulcanized and comprise sulfur crosslinks;

wherein the synthetic polyisoprene particles comprise a rare earth catalysed polyisoprene material that comprises:

a cis-1,4 isomer content of greater than 97.0% by weight; a trans-1,4 isomer content of 1% by weight or less; and a 3,4 isomer content of 1% by weight or less.

8. The condom of claim 7, wherein the elastomeric layer forms an open end, a closed end, and a tubular sheath extending from the closed end to the open end.

9. The condom of claim 7, wherein the rare earth catalysed polyisoprene material comprises a branched macro-structure.

10. The condom of claim 7, wherein the elastomeric layer comprises a post-vulcanized structure having a molecular weight between crosslinks (Mc) of: less than about: 10500, 10250, 10000, 9750, 9500, 9250, 9000, 8800, 8600, 8400, 8200, 8000, 7800, 7600, 7400, 7200, 7000, 6900, 6800, 6700, 6600, or 6550 g/mol; or less than about 6,540 g/mol.

11. The condom of claim 7, wherein the synthetic polyisoprene particles have a maximum median particle diameter of approximately from 1 micrometre.

* * * * *